(12) United States Patent
Grossman (10) Patent No.: US 6,271,228 B1
(45) Date of Patent: Aug. 7, 2001

(54) BLOOD PRESSURE STABILIZATION DURING HEMODIALYSIS

(75) Inventor: Eric B. Grossman, Hasting-on-Hudson, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/800,836

(22) Filed: Mar. 7, 2001

Related U.S. Application Data (60) Provisional application No. 60/200,439, filed on Apr. 28, 2000.

(51) Int. Cl.⁷ .................. A61K 31/535; A61K 31/505
(52) U.S. Cl. .......................... 514/234.2; 514/258
(58) Field of Search .................. 514/258, 234.2

(56) References Cited

U.S. PATENT DOCUMENTS

| | | | | |
|---|---|---|---|---|
| 5,250,534 | * | 10/1993 | Bell et al. | 514/258 |
| 5,272,147 | * | 12/1993 | Bell et al. | 514/234.2 |
| 5,346,901 | * | 9/1994 | Bell et al. | 514/258 |

\* cited by examiner

*Primary Examiner*—Raymond Henley, III
(74) *Attorney, Agent, or Firm*—Peter C. Richardson; Gregg C. Benson; Arlene K. Musser (57) ABSTRACT

A method for stabilizing blood pressure during hemodialysis is described which uses a phosphodiesterase inhibitor, in particular, a cGMP $PDE_v$ inhibitor in the treatment of humans.

20 Claims, 3 Drawing Sheets

BLOOD PRESSURE STABILIZATION DURING HEMODIALYSIS

This application claims the benefit of U.S. Provisional Patent Application No. 60/200,439, filed Apr. 28, 2000, incorporated in its entirety herein by reference.

FIELD OF THE INVENTION

This invention relates to hemodialysis treatment, particularly to the stabilization of blood pressure during hemodialysis.

BACKGROUND

Chronic renal failure (CRF) may result from any major cause of renal dysfunction. The most common cause of end-stage renal discease is diabetic nephropathy, followed by hypertensive nephroangiosclerosis and various primary and secondary glomerulopathies. The functional effects of CRF can be categorized as diminished renal reserve, renal insufficiency (failure), and uremia.

Lassitude, fatigue, and decreased mental acuity often are the first manifestations of uremia. In addition, other symptoms of CRF include neuromuscular features, anorexia, nausea, vomiting, stomatitis, an unpleasant taste in the mouth, malnutrition, GI ulceration, bleeding, cardiomyopathy (hypertensive, ischemic), and ultimately congestive heart failure or dependent edema.

Treatments for CRF include protein restriction, ACE inhibitors, possibly angiotensin receptor blockers, and meticulous attention to diet as CRF progresses from moderate to end-stage disease. When conventional therapy is no longer effective, the patient is considered to have end-stage renal disease (ESRD) and long-term dialysis or transplantation is an option. Most physicians agree that uremic symptoms (nausea, vomiting, anorexia, fatigability, diminished sensorium) and signs (pericardial friction rub, refractory pulmonary edema, metabolic acidosis, foot or wrist drop, asterixis) necessitate urgent dialysis.

Dialysis is the process of removing toxins directly from the blood (hemodialysis) or indirectly via peritoneal fluid (peritoneal dialysis) using diffusion across a semipermeable membrane. Simultaneous ultrafiltration is usually accomplished to remove accumulated fluid ordinarily excreted by functioning kidneys. A dialysis regimen for ESRD should improve the patient's ability to perform activities of daily living, improve comfort, allow the patient to eat a reasonable diet, help maintain a normal blood pressure, and prevent progression of uremic neuropathy. Most ESRD patients require hemodialysis thrice weekly to maintain a state of well-being. Early treatment typically takes three to five hours in adults and three to four hours in children. Blood is removed from the patient via a suitable vascular access and pumped to the membrane unit. The dialysate compartment of the membrane unit is under negative pressure relative to the blood compartment, which permits hydraulic ultrafiltration of excess total body fluid across the membrane. Dialyzed blood is returned to the patient through tubing with an air embolus protector. The most common complications during hemodialysis are, in descending order of requency, hypotention (20–30% of dialyses), cramps (5–20%), nausea and vomiting (5–15%), headache (5%), chest pain (2–5%), back pain (2–5%), itching (5%), and fever and chills (<1%).

Hypotension during dialysis is a very common event and is primarily a reflection of the large amount of fluid relative to the plasma volume that is removed during an average dialysis session. Maintenance of blood volume during dialysis depends on rapid refilling of the blood compartment from surrounding tissue spaces. A decrease in the blood volume can result in decreased cardiac filling, which in turn can cause reduced cardiac output and, ultimately, hypotension.

In addition, hypotension maybe related to lack of vasoconstriction. Blood volume depletion causes a state in which cardiac output is limited by cardiac filling. Any minor decrease in peripheral vascular resistance or decrease in cardiac filling can precipitate hypotension, because the cardiac output cannot increase in a compensatory manner. Under conditions of decreased cardiac filling, increases in heart rate have little effect on cardiac output. The hypotension may also relate to cardiac factors such as diastolic dysfunction, heart rate and contractility. In addition, it has been suggested that nitric oxide may play a role in hypotension. Yokokawa, Joji, et. al., *Increased Nitric Oxide Production in Patients with Hypotension during Hemodialysis,* Ann. Intern. Med. 1995; 123: 35–37; Lin, Shih-Hua, et. al., *Increased Nitric Oxide Production in Hypotensive Hemodialysis Patients,* ASAIO Journal 1996; 42 no. 5: M895–M899; Rysz, Jacek, et al., *Nitric Oxide Release in the Peripheral Blood During Hemodialysis,* Kidney International, 1997; 51; 294–300; Nishimura, Masato, et. al., *Enhanced Production of Nitric Oxide May be Involved in Acute Hypotension During Maintenance Hemodialysis,* American Journal of Kidney Diseases, 1998, 31 no 5; 809–817. Management of the acute hypotensive patient includes placement of the patent in the Trendelenburg position (if respiratory status allows this). A bolus of 0.9% saline (100 ml or more as necessary) may be rapidly administered through the venous blood line. The ultrafiltration rate may also be reduced to as near zero as possible. Ultrafiltration can be resumed (at a slower rate, initially) once vital signs have stabilized. As an alternative to 0.9% saline, hypertonic saline, glucose, mannitol, or albumin solutions can be used to treat the hypotensive episode.

While hypotension remains the most prevalent side effect of hemodialysis and although its incidence has diminished with the advent of more advanced dialysis technology, the management treatments described above are not wholly satisfactory. For example, they include interruption of dialysis for a period to allow for blood pressure normalization. Thus, there is a continuing need for an alternative treatment for hypotension consequent to hemodialysis.

SUMMARY OF THE INVENTION

This invention is directed to a method of stabilizing blood pressure during hemodialysis comprising administering to a mammal in need of such treatment a therapeutically effective amount of a compound which is a phosphodiesterase (PDE) inhibitor. Preferably the PDE inhibitor is a cGMP PDE inhibitor. It is especially preferred that the cGMP PDE inhibitor is selective for the cGMP $PDE_v$ isoenzyme. One preferred cGMP $PDE_v$ inhibitor is sildenafil (a preferred salt being the citrate salt).

Preferably the mammal is a human (male or female). Typically about 0.01 mg/kg/day to about 100 mg/kg/day of a cGMP $PDE_v$ inhibitor may be administered.

It is preferred that about 0.1 mg/kg/day to about 2 mg/kg/day of a cGMP $PDE_v$ inhibitor is administered. It is also preferred that about 0.05 mg/kg/day to about 1 mg/kg/day of a cGMP $PDE_v$ inhibitor is administered parenterally. It is most preferred that about 25 mg/kg/day to about 75 mg/kg/day sildenafil citrate is administered orally.

Preferably the cGMP $PDE_v$ inhibitor is administered about 30 minutes to about 12 hours prior to initiation of hemodialysis and it is especially preferred that the cGMP PDE$_v$ inhibitor is administered orally about 30 minutes to about 2 hours prior to hemodialysis.

Preferred cGMP PDE inhibitors include 3-ethyl-5-[2-(2-methoxyethoxy)-5-(4-methylpiperazin-1-ylsulphonyl) pyridin-3-yl]-2-(pyridin-2-yl)methyl-2,6-dihydro-7H-pyrazolo[4,3-d]pyrimidin-7-one;

3-ethyl-5-[5-(4-ethylpiperazin-1-ylsulphonyl)-2)2-methoxyethoxy)pyridin-3-yl]-2-(pyridin-2-yl)methyl-2, 6-dihydro-7H-pyrazolo[4,3-d]pyrimidin-7-one;

3-ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one;

5-[2-(2-methoxyethyoxy)-5-(4-methylpiperazin-1-ylsulphonyl)pyridin-3-yl]-3-n-propyl-2-(pyridin-2-yl) methyl-2,6-dihydro-7H-pyrazolo[4,3-d]pyrimidin-7-one;

5-[5-(4-ethylpiperazin-1-ylsulphonyl)-2-(2-methoxyethoxy) pyridin-3-yl]-3-n-propyl-2-(pyridin-2-yl)methyl-2,6-dihydro-7H-pyrazolo[4,3-d]pyrimidin-7-one;

(+)-3-ethyl-5-[5-(4-ethylpiperazin-1-ylsulphonyl)-2-(2-methoxy-1(R)-methylethoxy)pyridin-3-yl]-2-methyl-2,6-dihydro-7-Hpyrazolo[4,3-d]pyrimidin-7-one;

3-ethyl-5-[5-(4-ethylpiperazin-1-ylsulphonyl)-2-(2-methoxy-1(R)-methylethoxy)pyridin-3-yl]-2-(6-methylpyridin-2-yl)methyl-2,6-dihydro-7H-pyrazolo[4, 3-d]pyrimidin-7-one;

5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one;

5-[2-i-butoxy-5-(4-ethylpiperazin-1-ylsulphonyl)pyridin-3-yl]-2,3-diethyl-2,6-dihydro-7H-pyrazolo[[4,3-d] pyrimidin-7-one; 5-[2-ethoxy-5-(4-ethylpiperazin-1-ylsulphonyl)pyridin-3-yl]-3-ethyl-2-[1-pyridin-2-yl) ethyl]2,6-dihydro-7H-pyrazolo[4,3-d]pyrimidin-7-one or the pharmaceutically acceptable salts, hydrates or solvates thereof.

In another aspect of this invention, hemodialysis occurs with a dialyzer or dialysis tubing that is internally rinsed with a solution of a cGMP PDE$_v$ inhibitor.

In yet another aspect of this invention, a CGMP PDE$_v$ inhibitor is administered over substantially the whole time period of hemodialysis.

In yet another aspect of this invention, the administration of the amount of the cGMP PDE$_v$ inhibitor is titrated to the blood pressure of the mammal e.g., human.

DEFINITIONS

By "pharmaceutically acceptable" it is meant the carrier, diluent, excipients, and/or salt must be compatible with the other ingredients of the formulation, and not deleterious to the recipient thereof.

The expression "pharmaceutically-acceptable salt" refers to for example, nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate. The expression also refers to for example, nontoxic cationic salts such as (but not limited to) sodium, potassium, calcium, magnesium, ammonium or protonated benzathine (N, N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention are also included.

Other features and advantages will be apparent from the description and claims which describe the invention and from the accompanying drawings.

DETAILED DESCRIPTION OF THE INVENTION

Cyclic guanosine 3',5'-monophosphate phosphodiesterase (cGMP PDE) inhibitors are widely known as cardiovascular agents for the treatment of conditions such as angina, hypertension, and congestive heart failure. U.S. Pat. No. 5,250,534, incorporated herein by reference, discloses a class of cyclic guanosine 3'5'-monophosphate (cGMP) phosphodiesterase type 5 (PDE5) inhibitors useful in the treatment of, for example, angina. One member of this class is sildenafil, which has two chemical names: 1-[[3-(6,7-dihydro-1-methyl-7-oxo-3-propyl-1 H-pyrazolo[4,3-d] pyrimidin-5-yl)4-ethoxyphenyl]sulfonyl]-4-methylpiperazine and 5-[2-ethoxy-5-(4-methylpiperazinylsulphonyl)phenyl]-1-methyl-3-n-propyl-1,6-dihydro-7H-pyrazolo[4,3-d]pyrimidin-7-one. Sildenafil citrate is sold under the tradename Viagra® by Pfizer Inc. and indicated for the treatment of erectile dysfunction. *Physician's Desk Reference* 2424–2426 (53$^{rd}$ ed. 1999). By slowing the rate of cGMP breakdown, sildenafil enhances the vasodilatory effect of naturally produced NO.

Patients undergoing hemodialysis typically suffer from a variety of comorbidity symptoms including those described in the background. In addition, some of the patients experience sexual dysfunction. The use of sildenafil citrate for the treatment of erectile dysfunction in such patients has been studied and found to be effective in small pilot trials. The present invention recognizes other features and advantages of sildenafil citrate which are described in more detail below and in the accompanying drawings.

A clearer understanding of this invention may be achieved by an understanding of the phrase "stabilization of blood pressure during hemodialysis". The term stabilization is meant to include the maintenance of blood pressure (whether diastolic or systolic) close to the level exhibited by the patient prior to the initiation of the hemodialysis therapy. It is know that the patients blood pressure response to hemodialysis is likely to be highly dependent on the volume of fluid removed for any specific hemodialysis treatment. While it is difficult to assign a numerical value to the stabilization, preferably this stabilization is within 15% of the norm for the individual patient (assuming a set volume of fluid is withdrawn) although it is understood that patients may still experience hypotensive episodes. It is especially preferred that stabilization is within 10% of the norm for the individual patient and even more preferred that it is within 5% of the norm. Further, the period of normalization lasts typically about four to about eight hours subsequent to administration of the compound.

Any phosphodiesterase (PDE) inhibitor may be used in the methods of this invention. As the PDE inhibitor, CGMP PDE inhibitors are preferred. CGMP PDE inhibitors which are selective for cGMP PDEs rather than cyclic adenosine 3',5'-monophosphate phosphodiesterases (cAMP PDEs) and/or which are selective inhibitors of the cGMP $PDE_v$ isoenzyme are particularly preferred. Such particularly preferred cGMP PDE inhibitors are disclosed in U.S. Pat. Nos. 5,250,534, 5,346,901, 5,272,147, and in the international patent application published as WO 94/28902 designating, inter alia, the U.S., each of which is incorporated herein by reference.

The cGMP PDE inhibition of a compound can be determined by standard assays known to the art, for example as disclosed in U.S. Pat. No. 5,250,534, incorporated herein by reference. Again, compounds which are selective inhibitors of cGMP PDE relative to cAMP PDE are preferred, and determination of such compounds is also taught in U.S. Pat. No. 5,520,534. The cGMP $PDE_v$ inhibition of a compound can be determined by standard assays known in the art, for example as disclosed in WO 94/28902.

Reference to PDE inhibitors both in this disclosure and the appendant claims, shall at all times be understood to include all active forms of such agents, including the free form thereof (e.g., the free acid or base form) and also all pharmaceutically acceptable salts, prodrugs, polymorphs, hydrates, solvates, isomers, stereoisomers (e.g. diastereomers and enantiomers), tautomers, and so forth. Active metabolites of the PDE inhibitors in any form, are also included.

Preferred cGMP PDE inhibitors include sildenafil which has the structure:

and pharmaceutically acceptable salts thereof, and the compound having the structure:

and pharmaceutically acceptable salts thereof. The second compound is disclosed, for example, in U.S. Pat. Nos. 5,272,147 and 5,426,107, both incorporated herein by reference.

Other preferred cGMP PDE inhibitors include 3-ethyl-5-[2-(2-methoxyethoxy)-5-(4-methylpiperazin-1-ylsulphonyl) pyridin-3-yl]-2-(pyridin-2-yl)methyl-2,6-dihydro-7H-pyrazolo[4,3-d]pyrimidin-7-one;
3-ethyl-5-[5-(4-ethylpiperazin-1-ylsulphonyl)-2)2-methoxyethoxy)pyridin-3-yl]-2-(pyridin-2-yl)methyl-2, 6-dihydro-7H-pyrazolo[4,3-d]pyrimidin-7-one;
3-ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one;
5-[2-(2-methoxyethyoxy)-5-(4-methylpiperazin-1-ylsulphonyl)pyridin-3-yl]-3-n-propyl-2-(pyridin-2-yl) methyl-2,6-dihydro-7H-pyrazolo[4,3-d]pyrimidin-7-one;
5-[5-(4-ethylpiperazin-1-ylsulphonyl)-2-(2-methoxyethoxy) pyridin-3-yl]-3-n-propyl-2-(pyridin-2-yl)methyl-2,6-dihydro-7H-pyrazolo[4,3-d]pyrimidin-7-one;
(+)-3-ethyl-5-[5-(4-ethylpiperazin-1-ylsulphonyl)-2-(2-methoxy-1(R)-methylethoxy)pyridin-3-yl]-2-methyl-2,6-dihydro-7-Hpyrazolo[4,3-d]pyrimidin-7-one;
3-ethyl-5-[5-(4-ethylpiperazin-1-ylsulphonyl)-2-(2-methoxy-1(R)-methylethoxy)pyridin-3-yl]-2-(6-methylpyridin-2-yl)methyl-2,6-dihydro-7H-pyrazolo[4,3-d]pyrimidin-7-one;
5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one;
5-[2-i-butoxy-5-(4-ethylpiperazin-1-ylsulphonyl)pyridin-3-yl]-2,3-diethyl-2,6-dihydro-7H-pyrazolo[[4,3-d] pyrimidin-7-one; 5-[2-ethoxy-5-(4-ethylpiperazin-1-ylsulphonyl)pyridin-3-yl]-3-ethyl-2-[1-pyridin-2-yl) ethyl]2,6-dihydro-7H-pyrazolo[4,3-d]pyrimidin-7-one;
5-[2-Ethoxy-5-(4-ethylpiperazin-1-ylsulphonyl)pyridin-3-yl]-3-ethyl-1-(2-methoxyethyl)-1,6-dihydro-7H-pyrazolo[4,3-d]pyrimidin-7-one; 3-Ethyl-5-[5-(4-ethylpiperazin-1-ylsulphonyl)-2-propoxyphenyl]-2-(pyridin-2-yl)methyl-2,6-dihydro-7H-pyrazolo[4,3-d] pyrimidin-7-one; 5-(2-ethoxy-5-(2-(4-morpholino)acetyl) phenyl)-1-methyl-3-propyl-1,6-dihydro-7H-pyrazolo[4, 3-d]pyrimidin-7-one or the pharmaceutically acceptable salts thereof.

A preferred pharmaceutically acceptable salt of sildenafil for use in this invention is the citrate salt.

Also preferred are compounds disclosed in PCT/EP95/00183, published as WO 95/19978 designating, inter alia, the United States, and herein incorporated by reference, the compounds disclosed therein have the formula (I)

and salts and solvates thereof, in which:
$R^0$ represents hydrogen, halogen or $(C_1-C_6)$alkyl,;
$R^1$ represents hydrogen, $(C_1-C_6)$alkyl, $(C_2-C_6)$alkenyl, $(C_2-C_6)$alkynyl, halo$(C_1-C_6)$alkyl, $(C_3-C_8)$cycloalkyl, $(C_3-C_8)$cycloalkyl$(C_1-C_3)$alkyl, aryl$(C_1-C_3)$alkyl or heteroaryl$(C_1-C_3)$alkyl;
$R^2$ represents an optionally substituted monocyclic aromatic ring selected from benzene, thiophene, furan and pyridine or an optionally substituted bicyclic ring attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and
$R^3$ represents hydrogen or $(C_1-C_3)$alkyl, or $R^1$ and $R^3$ together represent a 3- or 4-membered alkyl or alkenyl chain.

A preferred subset of compounds having formula Ia (also disclosed in WO 95/19978) includes compounds of the formula (Ia)

and salts and solvates thereof, in which:
$R^0$ represents hydrogen, halogen or $(C_1-C_6)$alkyl;
$R^1$ represents hydrogen, $(C_1-C_6)$alkyl, halo$(C_1-C_6)$alkyl, $(C_3-C_8)$cycloalkyl, $(C_3-C_8)$cycloalkyl$(C_1-C_3)$alkyl, aryl $(C_1-C_3)$alkyl or heteroaryl$(C_1-C_3)$alkyl; and
$R^2$ represents an optionally substituted monocyclic aromatic ring selected from benzene thiophene, furan and pyridine or an optionally substituted bicyclic ring attached to the rest of the molecule via one of the benene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen.

A specific compound within formula (I) is:
(6R, 12aR)-2,3,6,7,12,12a-hexahydro-2-methyl-6-(3,4-methylenedioxyphenyl)-pyrazino[2',1':6,1]pyrido[3,4-b]indole-1,4-dione.

The cGMP PDE inhibitors useful in this invention as PDE inhibitors may be widely chosen from among any of those already known to the art or subsequently discovered and/or hereafter developed. Suitable cGMP PDE inhibitors include those disclosed in any of the following U.S. patents, all of which are incorporated herein by reference:

a 5-substituted pyrazolo[4,3-d]pyrimidine-7-one as disclosed in U.S. Pat. No. 4,666,908;

a griseolic acid derivative as disclosed in any of U.S. Pat. Nos. 4,634,706, 4,783,532, 5,498,819, 5,532,369, 5,556,975, and 5,616,600;

a 2-phenylpurinone derivative as disclosed in U.S. Pat. No. 4,885,301;

a phenylpyridone derivative as disclosed in U.S. Pat. No. 5,254,571;

a fused pyrimidine derivative as disclosed in U.S. Pat. No. 5,047,404;

a condensed pyrimidine derivative as disclosed in U.S. Pat. No. 5,075,310;

a pyrimidopyrimidine derivative as disclosed in U.S. Pat. No. 5,162,316;

a purine compound as disclosed in U.S. Pat. No. 5,073,559;

a quinazoline derivative as disclosed in U.S. Pat. No. 5,147,875;

a phenylpyrimidone derivative as disclosed in U.S. Pat. No. 5,118,686;

an imidazoquinoxalinone derivative or its aza analog as disclosed in U.S. Pat. Nos. 5,055,465 and 5,166,344;

a phenylpyrimidone derivative as disclosed in U.S. Pat. No. 5,290,933;

a 4-aminoquinazoline derivative as disclosed in U.S. Pat. Nos. 5,436,233 or 5,439,895;

a 4,5-dihydro-4-oxo-pyrrolo[1,2-a]quinoxaline derivative as disclosed in U.S. Pat. No. 5,405,847;

a polycyclic guanine derivative as disclosed in U.S. Pat. No. 5,393,755;

a nitogenous heterocyclic compound as disclosed in U.S. Pat. No. 5,576,322;

a quinazoline derivative as disclosed in U.S. Pat. No. 4,060,615; and a 6-heterocyclyl pyrazolo[3,4-d]pyrimidin-4-one as disclosed in U.S. Pat. No. 5,294,612.

Other disclosures of cGMP PDE inhibitors include the following, all of which are herein incorporated by reference:
*European patent Application (EPA) publication no.* 0428268;
European patent 0442204;
International patent application publication no. WO 94/19351;
Japanese patent application 5-222000;
European Journal Of Pharmacology, 251, (1994), 1; and
International patent application publication no. WO 94/22855.

The starting materials and reagents for the above described compounds, are also readily available or can be easily synthesized by those skilled in the art using conventional methods of organic synthesis.

Some of the compounds useful for this invention have asymmetric carbon atoms and therefore are enantiomers or diastereomers. Diasteromeric mixtures can be separated into their individual diastereomers on the basis of their physical chemical differences by methods known per se, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

Many of the compounds useful for this invention are acidic and they form a salt with a pharmaceutically acceptable cation. Many of the compounds useful for this invention are basic and they form a salt with a pharmaceutically acceptable anion. All such salts are within the scope of this invention and they can be prepared by conventional methods. For example, they can be prepared simply by contacting the acidic and basic entities, usually in a stoichiometric ration, in either an aqueous, non-aqueous or partially aqueous medium, as appropriate. The salts are recovered either by filtration, by precipitation and non-solvent followed by filtration, by evaporation of the solvent, or, in the case of aqueous solutions, by lyophilization, as appropriate.

In addition, when the compounds useful for this invention form hydrates or solvates they are also within the scope of the invention.

The utility of the compounds useful for the methods of this invention (stabilization of blood pressure consequent to hemodialysis) in mammals (e.g., humans) is demonstrated by the activity of the compounds of this invention in the clinical protocol described below. The protocol also provides a means whereby the activities of the compounds useful for this invention can be compared to each other and with the activities of other known compounds. The results of these comparisons are useful for determining dosage levels in mammals, including humans, for the treatment of blood pressure stabilization consequent to hemodialysis.

Clinical Protocol

The study is a placebo controlled randomized crossover study conducted with a total of 3 study visits. The first study visit is for screening and includes administration of a complete medical history, physical examination, and laboratory examination and occurs no more than 2 weeks prior to the beginning of the first dosing phase. If the patient qualifies for the study, randomization to placebo or active drug first occurs. In the second visit the test compound is dosed 2 hours prior to hemodialysis. One week following the start of the first dosing phase (second visit) the patient is crossed over in the second dosing phase (third visit). Blood pressure (both systolic and diastolic) are measured as well as heart rate and the patient is followed for 42 to 48 hours following dosing. The patient undergoes a complete physical examination at the conclusion of the study.

The exact dose of the compound administered will, of course, differ depending on the specific compound prescribed, on the subject being treated, on the severity of the disease state, on the manner of administration and on the judgment of the prescribing physician. Thus, because of patient-to-patient variability, the dosages given below are a guideline and the physician may adjust doses of the compounds to achieve the treatment that the physician considers appropriate for the patient, male or female. In considering the degree of treatment desired, the physician must balance a variety of factors such as the age of the patient and the presence of other diseases or conditions (e.g., cardiovascular disease). In general, the PDE inhibitor will be administered in a range of from about 0.01 to about 100 mg/kg/day, preferably about 0.1 to about 2 mg/kg/day orally and preferably about 0.05 mg/kg/day to about 1 mg/kg/day parenterally. Typically the compound is administered about 30 minutes to about 12 hours, preferably about 30 minutes to about 2 hours prior to initiation of hemodialysis. The compound may also be administered by coating internally the dialysis tubing or dialysis machine with the compound (e.g., as a solution). Preferably, the compound is administered during the course of the hemodialysis after optional pre-administration of the compound as described above. The amount of compound delivered may also be titrated to the patients blood pressure during hemodialysis to provide optimum stabilization of blood pressure. One skilled in the art would know that the administration of Viagra and nitrates are contraindicated. A compound of this invention can be administered in any conventional oral, parenteral, rectal or transdermal dosage form, usually also together with a pharmaceutically acceptable vehicle, diluent or carrier.

For oral administration, a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents coloring agents, emulsifying agents and/or suspending agents, as well as such diluents such as water, ethanol, propylene glycol, glycerin and various like combinations thereof.

For purposes of parenteral administration, solutions in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0. 1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easter, Pa., 15$^{th}$ Edition (1975).

EXAMPLES

The study was a two-phase, randomized crossover, open-label study conducted with a total of 3 study visits. The first study visit was for screening and included administration of a complete medical history, physical examination, and laboratory examination. If the patient qualified for the study, randomization to study phase order occurred. The two phases were administered 1 to 2 weeks apart and involved dosing of Viagra® (sildenafil citrate) 50 mg by mouth. One phase dosed Viagra® (sildenafil citrate) 2 hours prior to hemodialysis; and the second phase dosed Viagra® (sildenafil citrate) 2 hours following hemodialysis. Hemodialysis lasted about three and one-half hours. Blood pressure (both systolic and diastolic) were measured as well as heart rate. The patient was followed for 42 to 48 hours following the dose of Viagra® (sildenafil citrate) during both phases of the study. The patient underwent a complete physical examination at the conclusion of the study.

Figure 1:
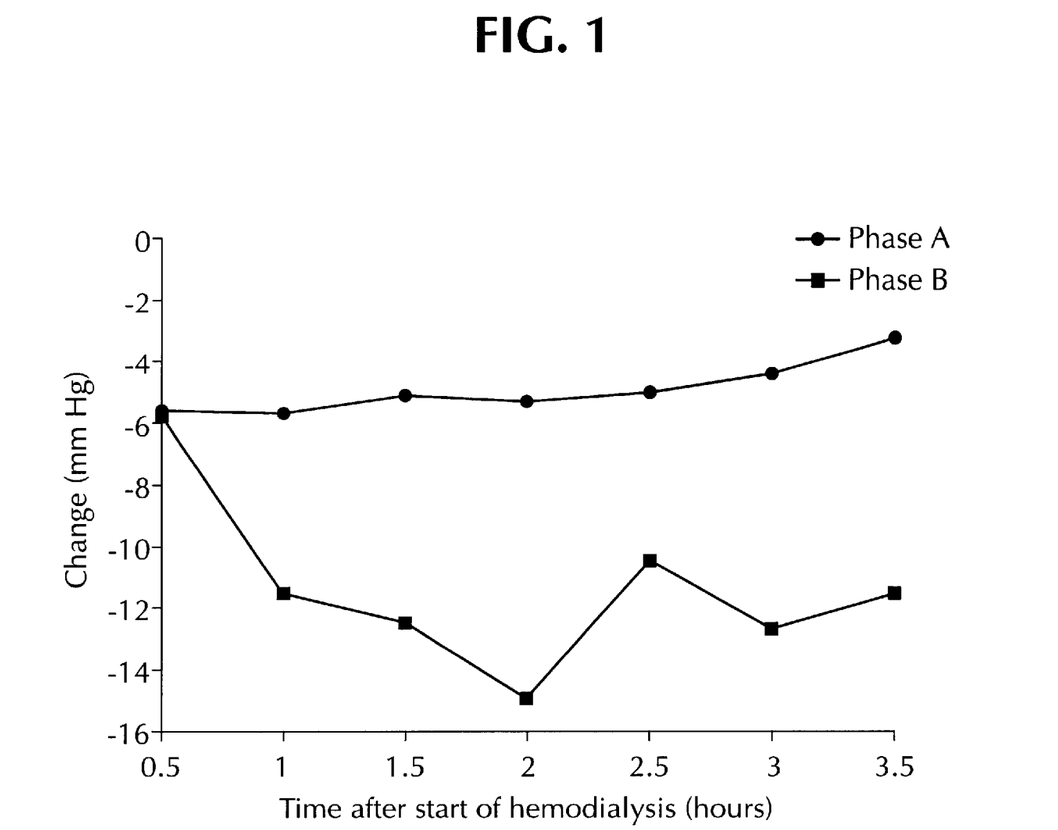
FIG. 1 is a systolic blood pressure graph of patients administered sildenafil citrate prior to hemodialysis vs. patients who had not been administered sildenafil citrate.
Figure 2:
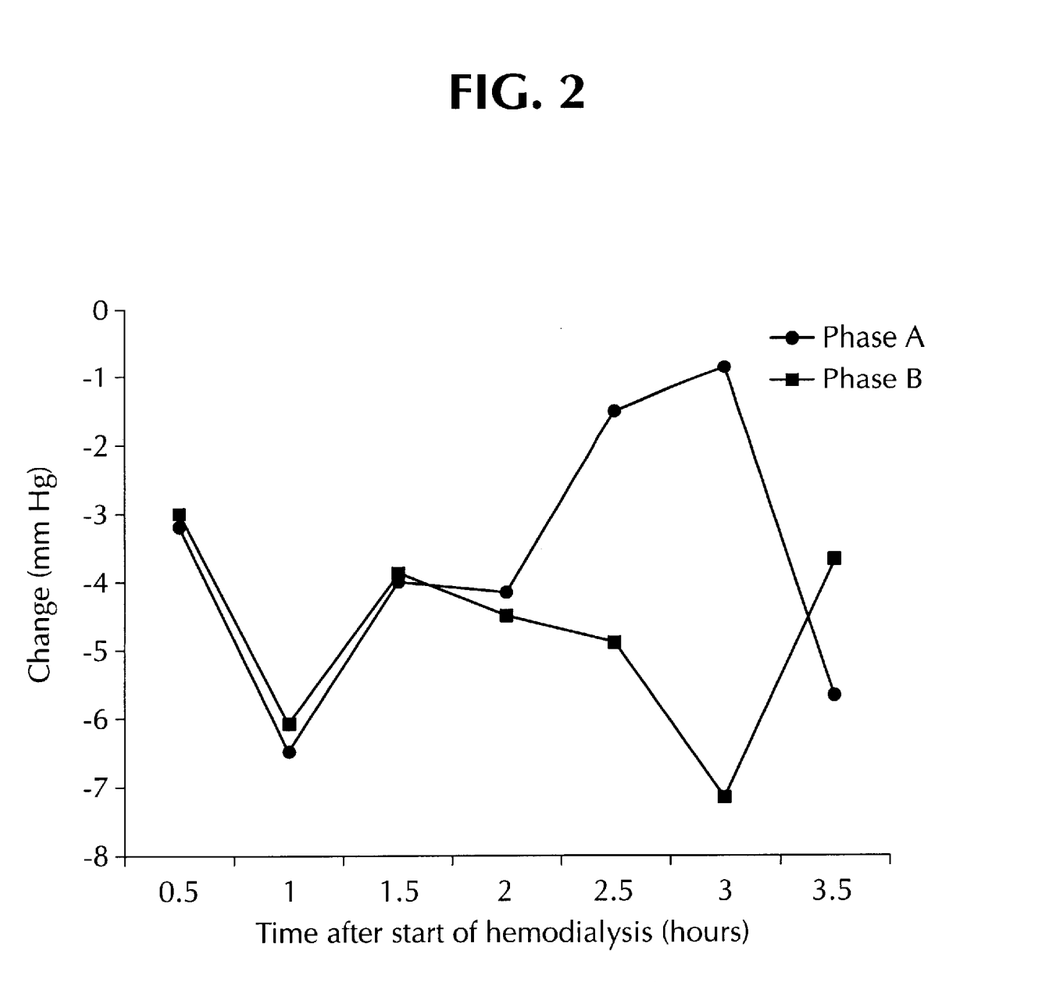
FIG. 2 is a diastolic blood pressure graph of patients administered sildenafil citrate prior to hemodialysis vs. patients who have not been administered sildenafil citrate.

The results are provided in FIGS. 1 and 2 and indicate that blood pressure was more stable during dialysis when sildenafil citrate was dosed before dialysis.

FIG. 1 details changes in systolic blood pressure during hemodialysis. Phase A describes changes in systolic blood pressure for those patients administered Viagra® two hours prior to hemodialysis. Phase B describes changes in systolic blood pressure for those patients who were not administered Viagra® prior to hemodialysis.

FIG. 2 details changes in diastolic blood pressure during hemodialysis. Phase A describes changes in diastolic blood pressure for those patients administered Viagra® two hours prior to hemodialysis. Phase B describes changes in diastolic blood pressure for those patients who were not administered Viagra® prior to hemodialysis.

Figure 3:
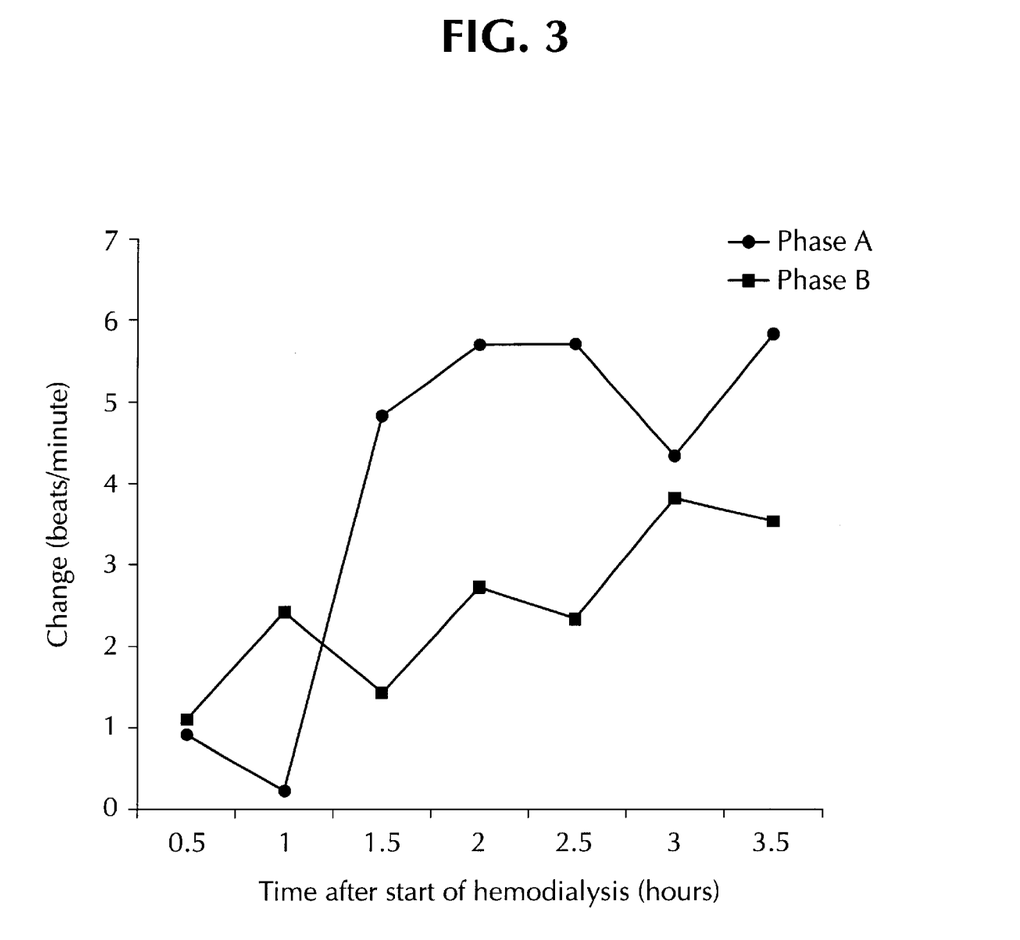
FIG. 3 is a heart rate graph of patients administered sildenafil citrate prior to hemodialysis vs. patients who had not been administered sildenafil citrate.

FIG. 3 details changes in heart rate during hemodialysis. Phase A describes changes in heart rate for patients administered Viagra® two hours prior to the start of hemodialysis. Phase B describes changes in heart rate for those patients who were not administered Viagra® prior to hemodialysis.

In this study while blood pressure was more stable in patients dosed with sildenafil prior to hemodialysis the number of hypotensive episodes was comparable for patients dosed with sildenafil citrate prior to or after hemodialysis. In this study a hypotensive episode was defined as any one of the following four conditions.

1. a systolic blood pressure decrease greater than 40 m Hg.
2. a systolic blood pressure of less than 90 mm Hg.
3. a diastolic blood pressure of less than 40 mm Hg.
4. a decrease in blood pressure causing symptoms.

What is claimed is:

1. A method of stabilizing blood pressure during hemodialysis comprising administering to a mammal in need of such treatment a therapeutically effective amount of a compound which is a PDE inhibitor.
2. The method of claim 2 wherein said PDE inhibitor is a cGMP PDE inhibitor and the mammal is a human.
3. The method of claim 1 wherein said cGMP PDE inhibitor is administered orally about 30 minutes to about 2 hours prior to hemodialysis.
4. The method of claim 2 wherein said cGMP PDE inhibitor is selective for the CGMP PDE$_v$ isoenzyme.
5. The method of claim 4 wherein said cGMP PDE inhibitor is sildenafil or a pharmaceutically acceptable salt thereof.
6. The method of claim 5 wherein said salt is the citrate salt.
7. The method of claim 2 wherein said CGMP PDE inhibitor has the structure 8. The method of claim 2 wherein said CGMP PDE inhibitor is
3-ethyl-5-[2-(2-methoxyethoxy)-5-(4-methylpiperazin-1-ylsulphonyl)pyridin-3-yl]-2-(pyridin-2-yl)methyl-2,6-dihydro-7H-pyrazolo[4,3-d]pyrimidin-7-one;
3-ethyl-5-[5-(4-ethylpiperazin-1-ylsulphonyl)-2)2-methoxyethoxy)pyridin-3-yl]-2-(pyridin-2-yl)methyl-2,6-dihydro-7H-pyrazolo[4,3-d]pyrimidin-7-one;
3-ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one;
5-[2-(2-methoxyethyoxy)-5-(4-methylpiperazin-1-ylsulphonyl)pyridin-3-yl]-3-n-propyl-2-(pyridin-2-yl)methyl-2,6-dihydro-7H-pyrazolo[4,3-d]pyrimidin-7-one;
5-[5-(4-ethylpiperazin-1-ylsulphonyl)-2-(2-methoxyethoxy)pyridin-3-yl]-3-n-propyl-2-(pyridin-2-yl)methyl-2,6-dihydro-7H-pyrazolo[4,3-d]pyrimidin-7-one;
(+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-Hpyrazolo[4,3-d]pyrimidin-7-one;
3-ethyl-5-[5-(4-ethylpiperazin-1-ylsulphonyl)-2-(2-methoxy-1(R)-methylethoxy)pyridin-3-yl]-2-(6-methylpyridin-2-yl)methyl-2,6-dihydro-7H-pyrazolo[4,3-d]pyrimidin-7-one;
5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one;
5-[2-i-butoxy-5-(4-ethylpiperazin-1-ylsulphonyl)pyridin-3-yl]-2,3-diethyl-2,6-dihydro-7H-pyrazolo[[4,3-d]pyrimidin-7-one;
5-[2-ethoxy-5-(4-ethylpiperazin-1-ylsulphonyl)pyridin-3-yl]-3-ethyl-2-[1-pyridin-2-yl)ethyl]2,6-dihydro-7H-pyrazolo[4,3-d]pyrimidin-7-one;
5-[2-Ethoxy-5-(4-ethylpiperazin-1-ylsulphonyl)pyridin-3-yl]-3-ethyl-1-(2-methoxyethyl)-1,6-dihydro-7H-pyrazolo[4,3-d]pyrimidin-7-one;
3-Ethyl-5-[5-(4-ethylpiperazin-1-ylsulphonyl)-2-propoxyphenyl]-2-(pyridin-2-yl)methyl-2,6-dihydro-7H-pyrazolo[4,3-d]pyrimidin-7-one;
5-(2-ethoxy-5-(2-(4-morpholino)acetyl)phenyl)-1-methyl-3-propyl-1,6-dihydro-7H-pyrazolo[4,3-d]pyrimidin-7-one; or a pharmaceutically acceptable salt, solvate, or hydrate thereof.

9. The method of claim 4 wherein about 0.01 mg/kg/day to about 100 mg/kg/day of the cGMP PDE$_V$ inhibitor is administered.

10. The method of claim 9 wherein about 0.1 mg/kg/day to about 2 mg/kg/day day of the cGMP PDE$_V$ inhibitor is administered orally.

11. The method of claim 9 wherein about 0.05 mg/kg/day to about 1/mg/kg/day day of the cGMP PDE$_V$ inhibitor is administered parenterally.

12. The method of claim 9 wherein the cGMP PDE$_V$ inhibitor is administered about 30 minutes to about 12 hours prior to initiation of hemodialysis.

13. The method of claim 2 wherein about 1 mg/kg/day to about 100 mg/kg/day of a cGMP PDE$_V$ inhibitor is administered orally about 30 minutes to about 2 hours prior to hemodialysis.

14. The method of claim 13 wherein the cGMP PDE$_V$ inhibitor is sildenafil citrate.

15. The method of claim 13 wherein the human is a male.

16. The method of claim 13 wherein the human is a female.

17. The method of claim 13 wherein about 25 mg/kg/day to about 75 mg/kg/day is administered.

18. The method of claim 2 wherein hemodialysis occurs with a dialyzer or dialysis tubing that is internally rinsed with a solution of a cGMP PDE$_V$ inhibitor.

19. The method of claim 2 wherein a CGMP PDE$_V$ inhibitor is administered over substantially the whole time period of hemodialysis.

20. The method of claim 19 wherein the administration of the amount of the CGMP PDEV inhibitor is titrated to the blood pressure of the human.

* * * * *